(12) United States Patent
Magnusson et al.

(10) Patent No.: US 9,528,940 B2
(45) Date of Patent: Dec. 27, 2016

(54) GUIDED-MODE RESONANCE SENSORS EMPLOYING ANGULAR, SPECTRAL, MODAL, AND POLARIZATION DIVERSITY FOR HIGH-PRECISION SENSING IN COMPACT FORMATS

(75) Inventors: Robert Magnusson, Storrs Mansfield, CT (US); Debra D. Wawro, Paradise, TX (US)

(73) Assignee: Board of Regents, University of Texas System, Austin, TX (US)

( * ) Notice: Subject to any disclaimer, the term of this patent is extended or adjusted under 35 U.S.C. 154(b) by 323 days.

(21) Appl. No.: 13/367,350

(22) Filed: Feb. 6, 2012

(65) Prior Publication Data
US 2012/0140208 A1    Jun. 7, 2012

Related U.S. Application Data

(60) Division of application No. 11/656,612, filed on Jan. 22, 2007, now Pat. No. 8,111,401, and a
(Continued)

(51) Int. Cl.
*G01B 9/02* (2006.01)
*G01N 21/77* (2006.01)
*G01N 21/25* (2006.01)

(52) U.S. Cl.
CPC ........ *G01N 21/7743* (2013.01); *G01N 21/253* (2013.01); *G01N 2021/7776* (2013.01)

(58) Field of Classification Search
CPC .............. G01N 21/253; G01N 21/7743; G01N 2021/7776
(Continued)

(56) References Cited

U.S. PATENT DOCUMENTS 5,337,183 A * 8/1994 Rosenblatt ................ G02F 1/01
                                                              359/245
5,455,178 A * 10/1995 Fattinger ...................... 436/164
(Continued)

FOREIGN PATENT DOCUMENTS

JP    2001-281284    10/2001
JP    2006-138842    6/2006
(Continued)

OTHER PUBLICATIONS

Eugene Hecht, Optics, Third Edition, published 1998, publisher Addison-Wesley, section 13.1.4.*

(Continued)

*Primary Examiner* — Michael A Lyons
(74) *Attorney, Agent, or Firm* — Shiells Law Firm P.C.; Theodore F. Shiells

(57) ABSTRACT

A guided mode resonance (GMR) sensor assembly and system are provided. The GMR sensor includes a waveguide structure configured for operation at or near one or more leaky modes, a receiver for input light from a source of light onto the waveguide structure to cause one or more leaky TE and TM resonant modes and a detector for changes in one or more of the phase, waveshape and/or magnitude of each of a TE resonance and a TM resonance to permit distinguishing between first and second physical states of said waveguide structure or its immediate environment.

18 Claims, 17 Drawing Sheets

Related U.S. Application Data continuation-in-part of application No. 12/115,484, filed on May 5, 2008, which is a division of application No. 11/305,065, filed on Dec. 16, 2005, now Pat. No. 7,400,399, which is a division of application No. 09/707,435, filed on Nov. 6, 2000, now Pat. No. 7,167,615.

(60) Provisional application No. 60/163,705, filed on Nov. 5, 1999, provisional application No. 60/164,089, filed on Nov. 6, 1999.

(58) Field of Classification Search
USPC .......... 356/300–334, 364, 369, 477, 480, 491,356/446; 385/12, 13; 422/82.11, 425; 435/288.7; 436/164
See application file for complete search history.

(56) References Cited

U.S. PATENT DOCUMENTS

| | | | |
|---|---|---|---|
| 5,738,825 A * | 4/1998 | Rudiger et al. ........... | 422/82.11 |
| 6,191,890 B1 * | 2/2001 | Baets .................... | G02B 5/1809 359/566 |
| 6,483,959 B1 * | 11/2002 | Singh ................. | G01N 21/0303 385/12 |
| 8,111,401 B2 * | 2/2012 | Magnusson et al. ........ | 356/480 |
| 2002/0037593 A1 * | 3/2002 | Craighead et al. ........... | 436/518 |
| 2003/0205681 A1 * | 11/2003 | Modlin ...................... | 250/458.1 |
| 2007/0054268 A1 | 3/2007 | Sutherland et al. | |
| 2008/0131885 A1 | 6/2008 | Pratilas et al. | |
| 2009/0024019 A1 | 1/2009 | Stein et al. | |
| 2009/0068668 A1 | 3/2009 | Duer | |

FOREIGN PATENT DOCUMENTS

| | | |
|---|---|---|
| JP | 2007-530973 | 8/2010 |
| WO | 2005-102020 | 11/2005 |

OTHER PUBLICATIONS

Rosenblatt, David et al. "Resonant Grating Waveguide Structures". IEEE Journal of Quantum Electronics, vol. 33, No. 11, Nov. 1997, pp. 2038-2059.*

Mateus C F R et al, "Ultracompact high-sensitivity labelfree biosensor using VCSEL", Proceedings of the SPIE—The International Society for Optical Engineering SPIE-INT. Soc. Opt. Eng USA, 20040622, vol. 5328, No. 1, ISSN 0277-786X, pp. 140-146, 1,3-4,6-7, 8,10 fig. 1, 3-4.

Challener W A et al, "A multilayer grating-based evanescent wave sensing technique", Sensors and Actuators B, Elsevier Sequoia S.A., Lausanne, CH, 20001115, vol. 71, No. 1-2, DOI:10.1016/S0925-4005 (00)00588-8, ISSN 0925-4005, pp. 42-46 9 fig. 1-2.

Shin D et al, "Theory and experiments of resonant waveguide gratings under Brewster incidence", Proceedings of the SPIE—The International Society for Optical Engineering SPIE-INT. Soc. Opt. Eng USA, 1999, vol. 3778, ISSN 0277-786X, pp. 31-39, 12 fig. 6-7.

Yih J-N. et al, "Optical Waveguide Biosensors Constructed With Subwavelength Gratings", Applied Optics, Optical Society of America, US, 20060320, vol. 45, No. 9, doi:DOI:10.1364/AO.45. 001938, ISSN 0003-6935, pp. 1938-1942, 1-12 fig. 3.

Ting-Chang Lee et al, "Novel GMR-based biochip", Proceedings of the SPIE—The International Society for Optical Engineering SPIE-INT. Soc. Opt. Eng USA, 2005, vol. 5702, No. 1, ISSN 0277-786X, pp. 160-167, 1-12 fig. 3-4.

Lukowiak A et al: "Optical properties of SiO2-TiO2 thin film waveguides obtained by the sol-gel method and their applications for sensing purposes", Optical Materials, Elsevier Science Publishers B.V. Amsterdam, NL, vol. 27, No. 9, Jul. 1, 2005 (Jul. 1, 2005), pp. 1501-1505, XP025328293, ISSN: 0925-3467, [retrieved on Jul. 1, 2005], DOI: 10.1016/J.Optmat.2005.01.007).

Parriaux O et al: "Sensitivity optimization of a grating coupled evanescent wave immunosensor", Sensors and Actuators B: Chemical: International Journal Devoted to Research and Development of Physical and Chemical Transducers, Elsevier S.A, Switzerland, vol. 29, No. 1, Oct. 1, 1995 (Oct. 1, 1995), pp. 289-292, XP004000884, ISSN: 0925-4005, DOI: 10.1016/0925-4005(95)01695-3.

* cited by examiner

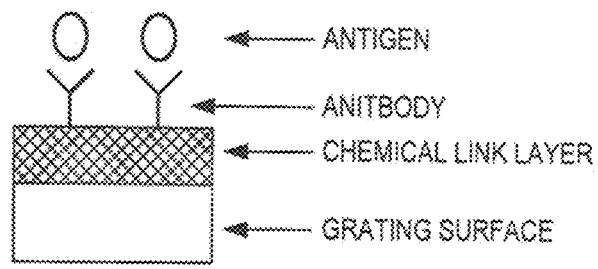
FIG. 1
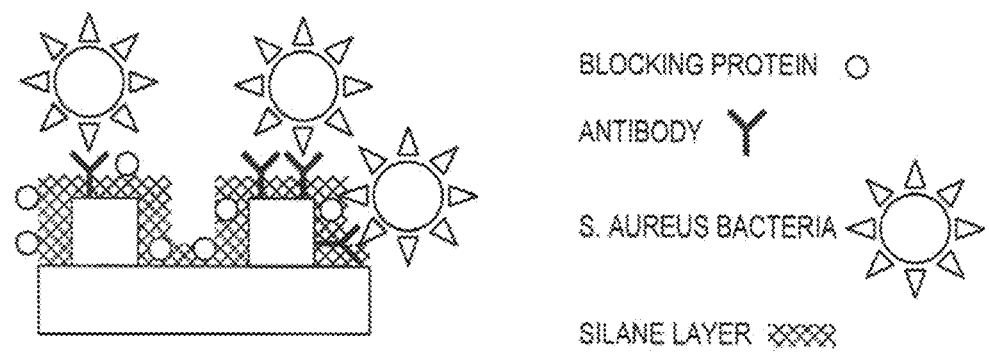
FIG. 2
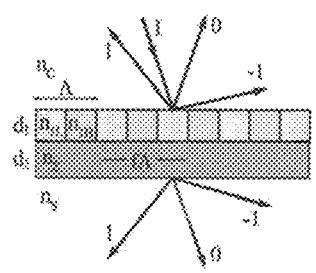 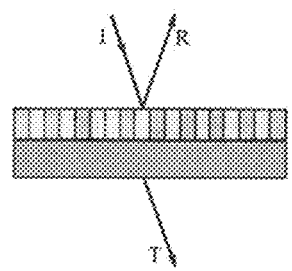 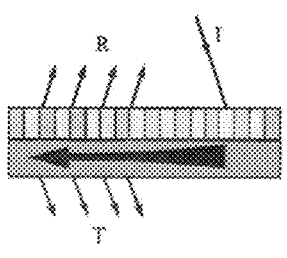
FIG. 3A  FIG. 3B  FIG. 3C

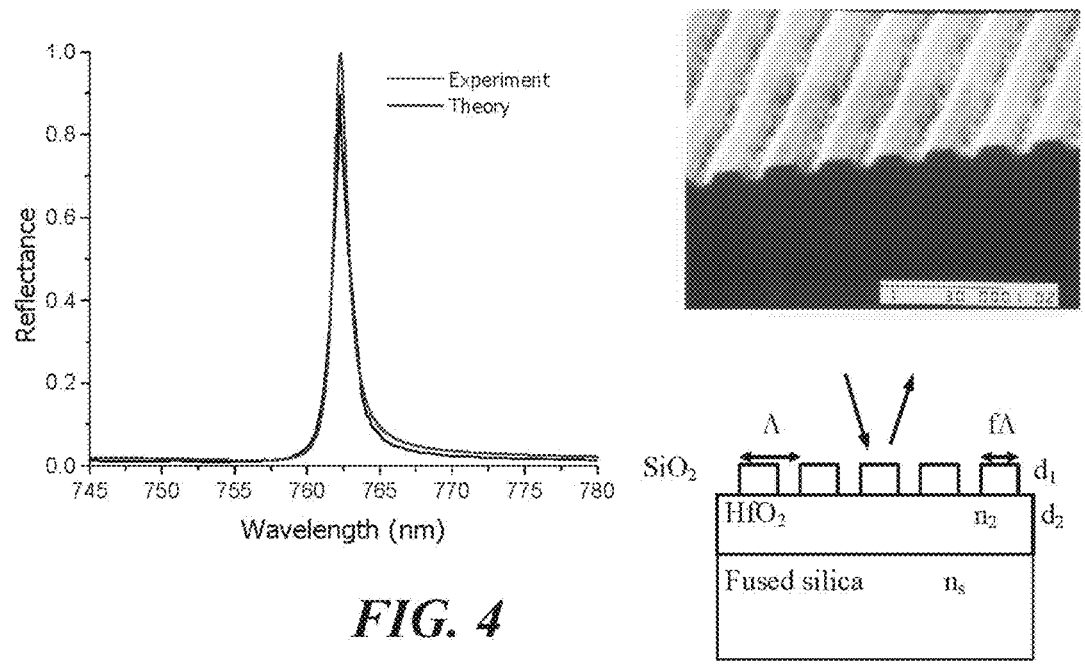
FIG. 4
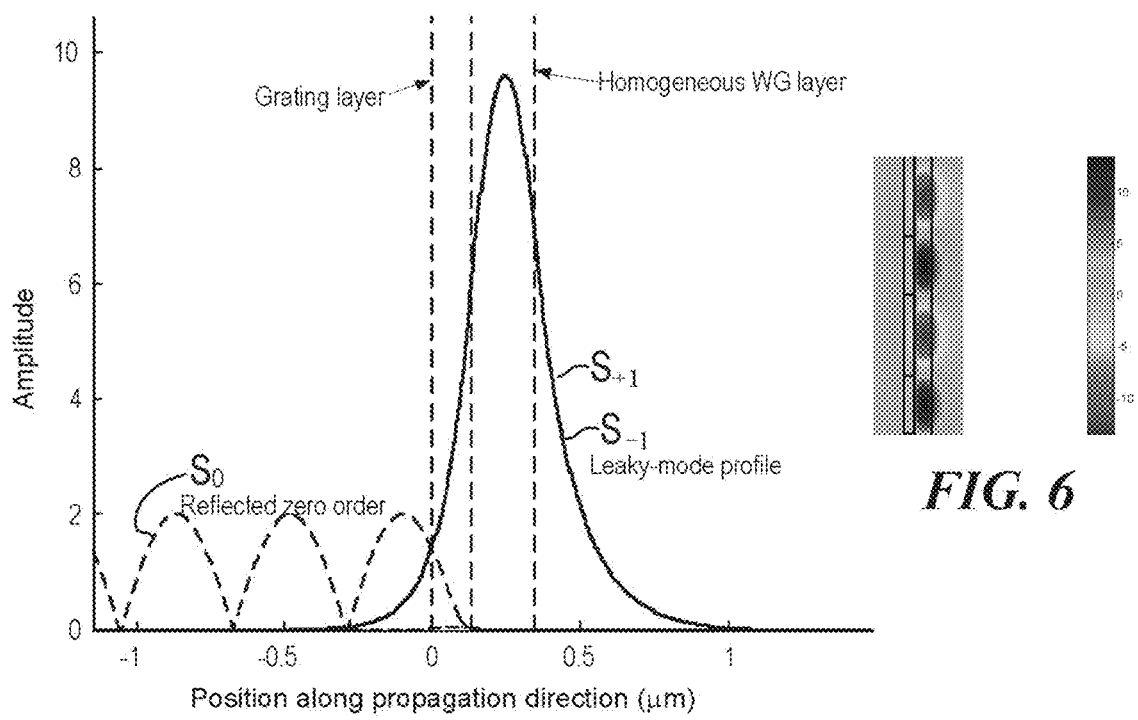
FIG. 5
FIG. 6

GUIDED-MODE RESONANCE SENSORS EMPLOYING ANGULAR, SPECTRAL, MODAL, AND POLARIZATION DIVERSITY FOR HIGH-PRECISION SENSING IN COMPACT FORMATS

PRIORITY

This application claims priority to, and is a divisional of, U.S. patent application Ser. No. 11/656,612, filed Jan. 22, 2007, being issued as U.S. Pat. No. 8,111,401, issue date of Feb. 7, 2012, the entire text of which is specifically incorporated by reference herein without disclaimer, and also claims priority to, and is a continuation-in-part of application Ser. No. 12/115,484 filed May 5, 2008, which was a division of application Ser. No. 11/305,065, filed Dec. 16, 2005, now U.S. Pat. No. 7,400,399 B2, issued Jul. 15, 2008, the entire text of which is specifically incorporated by reference herein without disclaimer, which was a division of application Ser. No. 09/707,435, filed on Nov. 6, 2000, now U.S. Pat. No. 7,167,615, issued Jan. 23, 2007, which claimed priority from provisional patent application Ser. Nos. 60/163,705 filed on Nov. 5, 1999 and 60/164,089, filed on Nov. 6, 1999,the entire text of which is specifically incorporated by reference herein without disclaimer

BACKGROUND OF THE DISCLOSURE

Field of the Invention

The present disclosure provides optical sensors operating with resonant leaky modes in periodic structures where angular, spectral, modal, and polarization diversity is advantageously applied for high-precision sensing in compact systems formats. Cross-referenced data sets thus obtained, fitted to numerical models, provide added degrees of precision and accuracy to enhance the quality of the sensing operation in a broad variety of applications.

Description of the Related Art

Numerous optical sensors for bio- and chemical detection have been developed commercially and in the research literature. Example devices include the surface plasmon resonance sensor, MEMS based cantilever sensors, resonant mirror, Bragg grating sensors, waveguide sensors, waveguide interferometric sensors, ellipsometry and grating coupled sensors. Of these, although dramatically different in concept, function, and capability, the surface plasmon resonance (SPR) sensor comes closest to the guided-mode resonance (GMR) sensor that is the subject of this disclosure. Both GMR and SPR sensors provide tag-free biochemical detection capability.

The term surface plasmon (SP) refers to an electromagnetic field induced charge-density oscillation that can occur at the interface between a conductor and a dielectric (for example, gold/glass interface). An SP mode can be resonantly excited by parallel-polarized TM polarized light (TM polarization refers to light with the electric field vector in the plane of incidence) but not with TE polarized light (the TE polarization refers to light where the TE vector is normal to the plane of incidence). Phase matching occurs by employing a metallized diffraction grating, or by using total internal reflection from a high-index material, such as in prism coupling, or an evanescent field from a guided wave. When an SPR surface wave is excited, an absorption minimum occurs in a specific wavelength band. While angular and spectral sensitivity is very high for these sensors, the resolution is limited by a broad resonant linewidth (~50 nm) and signal to noise ratio of the sensor response. Furthermore, as the operational dynamic range of the sensor is increased, the sensor sensitivity typically decreases. Since only a single polarization (TM) can physically be used for detection, change in refractive index and thickness cannot simultaneously be resolved in one measurement. This is particularly important in chemical sensor applications where binding kinetics include thickness changes at the sensor surface, while background refractive index can vary depending on analyte concentration. The disclosure provided herein can remedy some of the limitations of the present art.

Magnusson et al. discovered guided-mode resonance filters that were tunable on variation in resonance structure parameters. Thus, spectral or angular variations induced via layer thickness change or on change in refractive index in surrounding media or in device layers can be used to sense these changes. Wawro et al. discovered new GMR sensor embodiments as well as new possibilities of applications of these when integrated with optical fibers. There are also additional aspects of GMR sensors in various application scenarios.

SUMMARY OF THE DISCLOSURE

The present disclosure provides tag-free resonant sensors operating in reflection (that is, bandstop filter) or in transmission (that is, bandpass filter) wherein shaped angular spectra illuminate the GMR sensor element. These spectra simultaneously cover the incident angular ranges of interest with the received signal illuminating a linear detector array, or a CCD matrix, or other detectors, directly. On biomolecular attachment, or upon other variations of interest in the sensing region, these relatively narrow reflected or transmitted angular spectra alter their location on the detector matrix yielding a quantitative measurement of the molecular event of interest. Moreover, as the resonances arise as distinct TE and TM polarized responses, switching the input light polarization state can be applied to improve the quality of the sensing operation, or to measure additional parameters, by obtaining dual TE/TM resonance data. In addition, if desired, the input light can be spectrally tuned through a set of discrete wavelengths, thereby spatially shifting the locations of the measured spectra on the detectors providing possibilities of added enhancements of the precision of the measurement. Finally, sensor operation with multiple resonance peaks due to presence of multiple leaky waveguide modes can even further add to the measurement precision.

These operational modalities (angular, spectral, modal, and polarization) can be used in various combinations as needed. The sensors can be arranged into compact, high-density platforms requiring minimal reagent volumes. Therefore, as explained in this disclosure, this approach has numerous advantageous uses in practical sensor systems for high-precision measurement applications.

BRIEF DESCRIPTION OF THE FIGURES

To aid in the understanding of uses and implementations of the present disclosure for those having skill in the art, reference is made to numerous figures enclosed herein for clarity and expediency.

FIG. 1 shows an example of a biomolecular binding event on a surface of a biosensor.

FIG. 2 provides a schematic illustration of example bacterial detection.

FIG. 3 gives explanation of diffraction by resonant photonic-crystal waveguide structures with the zero-order condition and leaky mode resonance excitation clearly defined.

FIG. 4 provides a comparison between experiment and theory for a dielectric resonance element.

FIG. 5 shows the electric-field profile of the leaky mode at resonance for the element in FIG. 4.

FIG. 6 shows a computed instantaneous "snapshot" of the electromagnetic standing-wave pattern associated with the leaky mode in FIG. 5 at a maxima.

FIG. 12 shows calculated TE-polarization angular response of a GMR sensor for differing added thickness ($d_{bio}$) of biomaterials while

DETAILED DESCRIPTION OF EXEMPLARY EMBODIMENT

Background

Figure 7A:
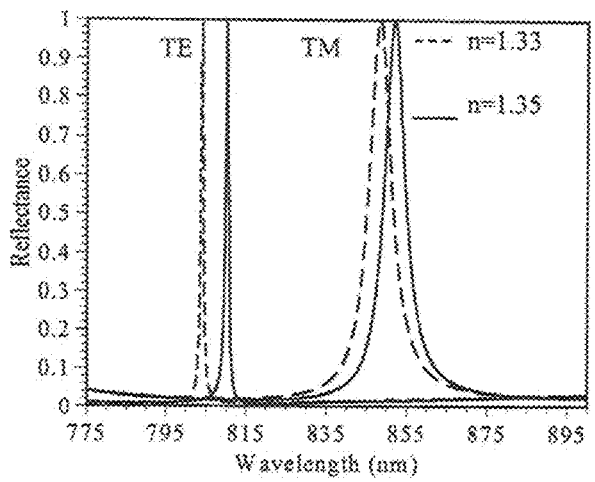
FIG. 7 illustrates a guided-mode resonance refractive index sensor employing TE and TM polarization diversity and depicts the structure producing the computed response.

It has been suggested by the inventors that by changing the refractive index and/or thickness of a resonant waveguide grating, its resonance frequency can be changed, or tuned. The present inventors have discovered that this idea has applications for biosensors as the buildup of the attaching biolayer can be monitored in real time, without use of chemical tags, by following the corresponding resonance wavelength shift with a spectrometer. Thus, the association rate between the analyte and its designated receptor can be quantified; in fact, the characteristics of the entire binding cycle, involving association, disassociation, and regeneration can be registered. Similarly, small variations in the refractive indices of the surrounding media, or in any of the waveguide-grating layers, can be measured. A new class of highly sensitive bio- and chemical sensors has thus been enabled. This sensor technology is broadly applicable to medical diagnostics, drug development, industrial process control, genomics, environmental monitoring, and homeland security.

To address one exemplary use in some detail, high performance, tag-free photonic-crystal GMR sensors are attractive for improved process control in drug development applications. This method is particularly useful owing to the enhancement in detection accuracy this sensor technology can provide to advance the process of drug development and screening. In this industry, millions of distinct chemical compounds need to be rapidly and accurately screened to determine which compounds bind to a particular protein or inhibit a target reaction. A purpose of high throughput screening (HTS) is to eliminate unpromising compounds before further development costs are incurred. Current HTS technologies typically use fluorescence or radioactive chemical tags as indicators of bioactivity. Due to the indicator-compound binding complexity, sometimes entirely new assays must be carefully designed utilizing new indicator technologies or reaction chemistries. There is increasing demand for novel sensor techniques that do not require labeling, and allow a wide range of materials to be selectively screened in real-time with minimal assay development (using readily available antibody-antigen, nucleic acids and other highly selective biomaterials). The capability to reduce errors from screening variables (such as temperature, and background fluid variations), as well as the ability to monitor binding dynamics in real time with simple array configurations are other desired features. High-precision GMR sensor methods, such as those disclosed here, can meet these needs for high throughput screening applications.

The sensor includes a periodic dielectric waveguide (also referred to as photonic crystal) in which resonant leaky modes are excited by an incident optical wave. Incident broadband light is efficiently reflected in a narrow spectral band whose central wavelength is highly sensitive to chemical reactions occurring at the surface of the sensor element. Interaction of a target analyte with a biochemical layer on the sensor surface yields measurable spectral shifts that directly identify the binding event without additional processing or foreign tags. A bio-selective layer (such as antibodies) can be incorporated on the sensor surface to impart specificity during operation as illustrated in FIG. 1. Sensor designs with sensitivities to thickness changes from the nanoscale (<0.1 angstroms) to as large as several microns have been analyzed. Thus, the same sensor technology can be used to detect binding events for small molecule drugs (<1 nm) and proteins (<10 nm), as well as larger bacterial analytes (>1 µm) as depicted schematically in FIG. 2. High resolution (obtained via narrow, well defined resonance peaks) and high sensitivities (associated with surface-localized leaky modes) provide a high probability of accurately detecting an event. Additionally, both major polarization states have independent resonant peaks to accurately sense a biomaterial binding event. This feature enables the capability to distinguish between average thickness changes and average density changes occurring at the sensor surface. Thus the sensor resonance response to a targeted chemical binding event (which includes a molecular conformational change) is distinguishable from unbound material settling on the sensor surface, thereby decreasing the occurrence of false positive readings.

GMR sensor technology is particularly versatile. The biomolecular reaction associated with an individual sensor, or sensor element in an array, can be simultaneously measured using the various properties of light including angular spectrum, wavelength spectrum, and polarization. Moreover, the GMR element itself can be designed to exhibit distinctly polarized resonances in a single peak due to a single leaky mode, say the $TE_0$ fundamental mode, or in multiple peaks originating in multiple leaky modes, for example, the $TE_0$, $TE_1$, and $TE_2$ modes. Such multiple modes will be made excitable, by proper sensor design, within the angular and wavelength spectral regions of interest. The electromagnetic field structure of the resonant mode can be configured such that the sensor operates with an evanescent tail in the sensing region or, alternatively, as a bulk mode sensor in which the leaky mode fully encloses the sensing region. Indeed, a particular operational leaky mode can be selected to maximize the light-measurand interaction to raise the detection sensitivity. For example, in a particular design, operation in the $TE_2$ mode may yield superior results over the $TE_0$ mode. The detection schemes thus summarized increase the amount and reliability of the information collected about the molecular event over those gathered by other means.

This sensor concept is broadly applicable in terms of materials, operating wavelengths, and design configurations. It is multifunctional as only the sensitizing surface layer needs to be chemically altered to detect different species. Operation in both air and liquid environments is possible. Due to the flexibility in materials selection, environmentally friendly dielectrics can be chosen in the fabrication of the sensor elements. Applicable materials include polymers, semiconductors, glasses, metals, and dielectrics.

Guided-Mode Resonance Effect

FIG. 3 shows the interaction of a thin-film waveguide grating (photonic crystal slab) and an incident plane wave. As the period Λ is reduced, higher-order propagating waves become increasingly cut off until the zero-order regime in FIG. 3(b) obtains. If the structure contains an appropriate waveguide, the first-order waves, now evanescent or cut off, can induce a resonance by coupling to a leaky mode. Indeed, the zero-order regime is often preferred as no energy is wasted in propagating higher-order diffracted waves such as those in FIG. 3(a).

Such thin-film structures containing waveguide layers and periodic elements (photonic crystals), under the correct conditions, exhibit the guided-mode resonance (GMR) effect. When an incident wave is phase-matched, by the periodic element, to a leaky waveguide mode shown in FIG. 3(c), it is reradiated in the specular-reflection direction with reflectance R as indicated in FIG. 3(c) as it propagates along the waveguide and constructively interferes with the directly reflected wave. Conversely and equivalently, the phase of the reradiated leaky mode in the forward, directly transmitted wave (transmittance T) direction in FIG. 3(c) is π radians out of phase with the direct unguided T wave, thereby extinguishing the transmitted light.

Experimental Bandstop Filter Example

FIG. 4 shows the measured and calculated spectral reflectance of a dielectric guided-mode resonance device. This device acts as a bandstop filter with the spectrum of interest reflected in a narrow band with relatively low sidebands. Although the theoretical calculation predicts 100% peak efficiency for a plane wave incidence, it is diminished in practice by various factors such as material and scattering losses, incident beam divergence, and the lateral device size; here the experimental peak is at 90% efficiency. This resonant element was fabricated by depositing an $HfO_2$ layer (~210 nm) and a $SiO_2$ layer (~135 nm) on a fused silica substrate (1-inch diameter). The SiO$_2$ grating was obtained by a series of processes including holographic recording of a photoresist mask grating (period of $\lambda$=446 nm) with an Ar+ UV laser ($\lambda$=364 nm) in a Lloyd mirror interference setup, development, deposition of ~10 nm Cr mask layer on top of the photoresist grating, lift-off of the photoresist grating, and subsequent reactive-ion etching of the SiO$_2$ layer with CF$_4$. The surface roughness evident in the SEM contributes to the reduction in peak efficiency.

Leaky-Mode Field Structure

In addition to the reflection/transmission properties of propagating electromagnetic waves, the near-field characteristics of resonant periodic lattices, including localization and field-strength enhancement, are of interest in sensor applications. The computed near field pattern associated with the fabricated example structure of FIG. 4 is presented in FIG. 5. Numerical results are obtained with rigorous coupled-wave analysis (RCWA) to provide quantitative information on relative field strengths and spatial extents associated with the near fields. As shown in FIG. 5, the zero-order $S_0$ wave ($S_0$ denotes the electric field of the zero order) propagates with reflected wave amplitude close to unity producing the standing-wave pattern shown by interference with the unit-amplitude input wave. Thus, at resonance, most of the energy is reflected back. Simultaneously, the first-order evanescent diffracted waves denoted $S_1$ and $S_{-1}$ constitute the counter-propagating leaky modes in this example. In this particular sensor, the maximum field value is located in the homogeneous layer with the evanescent tails gradually penetrating into the substrate and cover as clearly displayed in FIG. 5. FIG. 6 shows the standing wave pattern formed by the counter-propagating $S_{-1}$ and $S_{+1}$ waves at a certain instant of time. Since the $S_{\pm1}$ space harmonics correspond to localized waves, they can be very strong at resonance. Depending on the level of grating modulation ($\Delta\epsilon=n_H^2-n_L^2$), the field amplitude can range from ~×10× 1000 in the layer relative to the input wave amplitude which represents a large increase in local intensity I~$S^2$. The maximum amplitude of $S_1$ is approximately inversely proportional to modulation strength. The maximum amplitude of $S_1$ is approximately inversely proportional to modulation strength. In general, small modulation implies narrow linewidth $\Delta\lambda$ and a large resonator Q factor $Q=\lambda/\Delta\lambda$.

Exemplary Sensor Response and Sensitivity

Figure 7B:
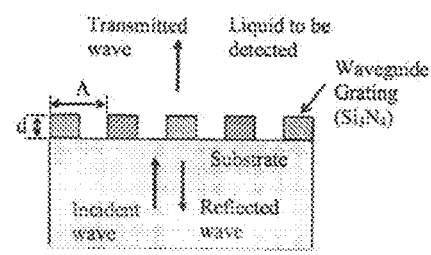
Figure 8:
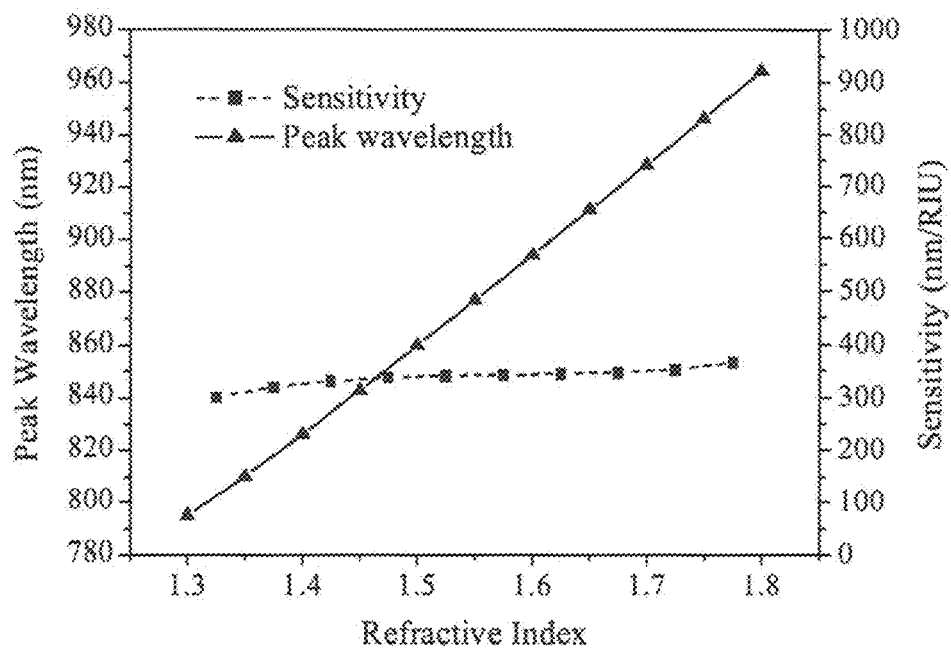
FIG. 8 shows corresponding TE-polarization resonance wavelength shift for large dynamic range sensing for the example in FIG. 7.
Figure 9:
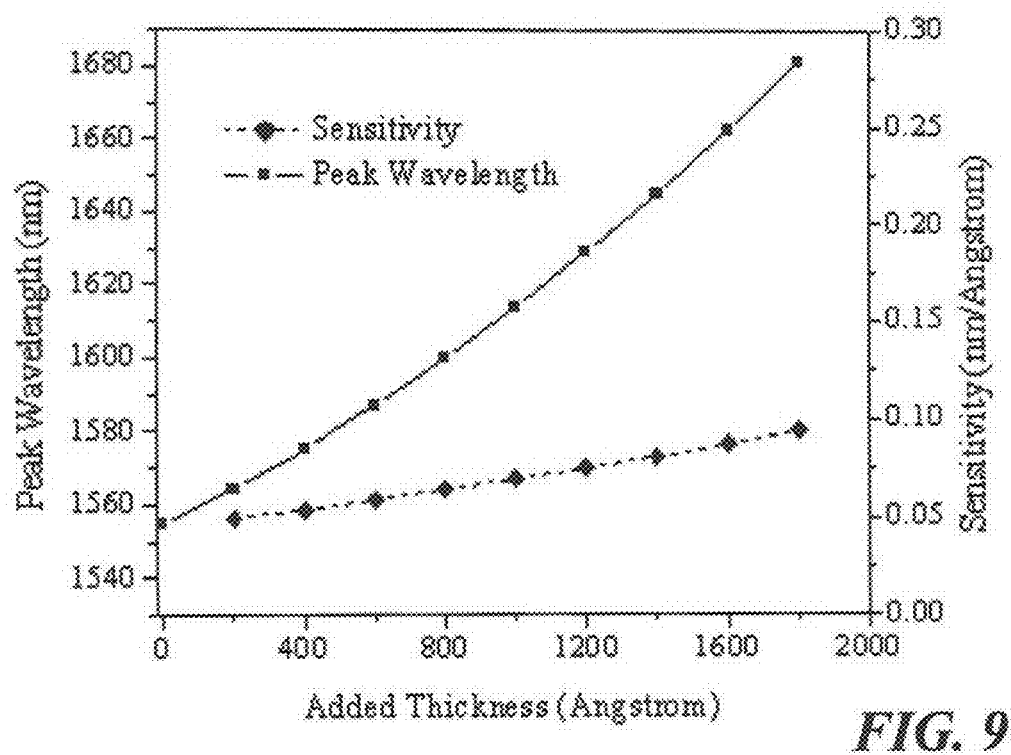
FIG. 9 illustrates thickness sensing in air.

The computed spectral response for a single-layer sensor designed for use in a liquid environment is provided in FIG. 7. This sensor can be fabricated with Si$_3$N$_4$ and patterned by plasma etching to create the diffractive layer. One-dimensional resonant waveguide grating structures have separate reflectance peaks for TE (electric vector normal to the page) and TM polarized incident waves. The calculation shows that this design can resolve an average refractive index change of $3\times10^{-5}$ refractive index units (RIU) assuming a spectrometer resolution of 0.01 nm. A nearly linear wavelength shift is maintained (FIG. 8) for a wide refractive index change of the medium in contact with the grating structure ($n_c=n_L$=1.3 to 1.8), making this a versatile sensor with a large dynamic range. The sensitivity of a biosensor is defined as the measured response (such as peak wavelength shift) for a particular amount of material that is detected. This indicates the maximum achievable sensitivity to the analyte under detection. Sensor resolution includes realistic component limitations such as spectroscopic equipment resolution, power meter accuracy, bioselective agent response, and peak shape or linewidth. Linewidth is the full width at half maximum (FWHM) of the reflected peak response. It affects the accuracy of spectroscopic sensors as a narrow line typically permits improved resolution of wavelength shifts; resonant waveguide grating sensors typically have narrow linewidths on the order of ~1 nm controllable by design. While resonant sensors can monitor tiny refractive index changes, they can also be used to detect thickness changes at the sensor surface, as the computed results in FIG. 9 show for realistic materials and wavelengths.

Exemplary Sensor Results

Figure 10:
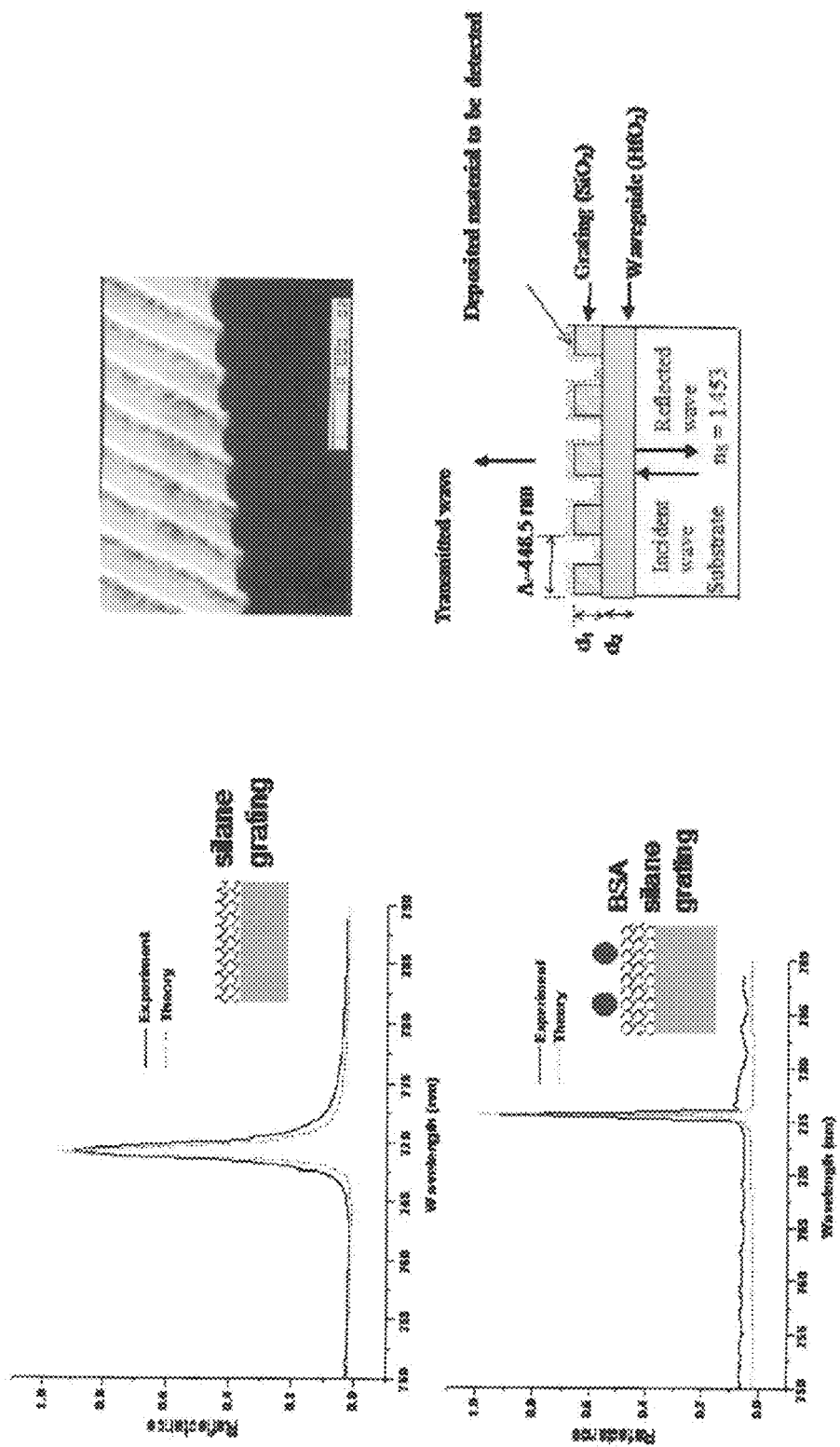
FIG. 10 provides measured GMR sensor spectral response in air for a TE-polarized (top, left) device surface modified with silane chemical linker (bottom, left). A scanning electron micrograph (SEM) is also shown (top, right) as well as a device model (bottom, left).

As exemplified in FIG. 10, the use of GMR sensor technology for biosensing applications has been investigated with protein binding studies in air utilizing a 2-layer resonant element illuminated at normal incidence. In this case, the clean grating surface is first chemically modified with amine groups by treating with a 3% solution of aminopropyltrimethoxysilane (Sigma) in methanol (FIG. 10 top, left). The device is then washed in a solution of bovine serum albumin (BSA, 100 mg/ml, Sigma) and a deposited 38 nm thick layer of BSA results in a reflected resonant peak spectral shift of 6.4 nm (FIG. 10 bottom, left). It is noted that minimal signal degradation results from the biomaterial layer on the sensor surface with reflectance remaining at ~90% before and after BSA attachment.

Fabrication of Resonant Sensor Elements by Contact Printing

Figure 11A:
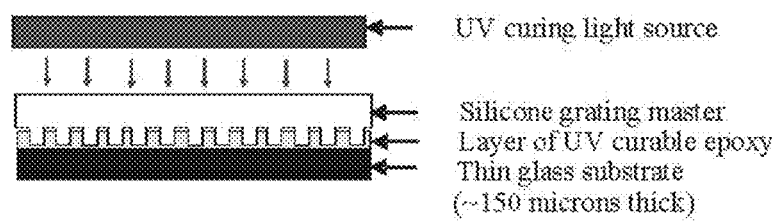
FIG. 11 depicts a submicron grating contact printing technique and an electron microscope picture of a 520-nm period grating contact printed in an optical adhesive medium.
Figure 11B:
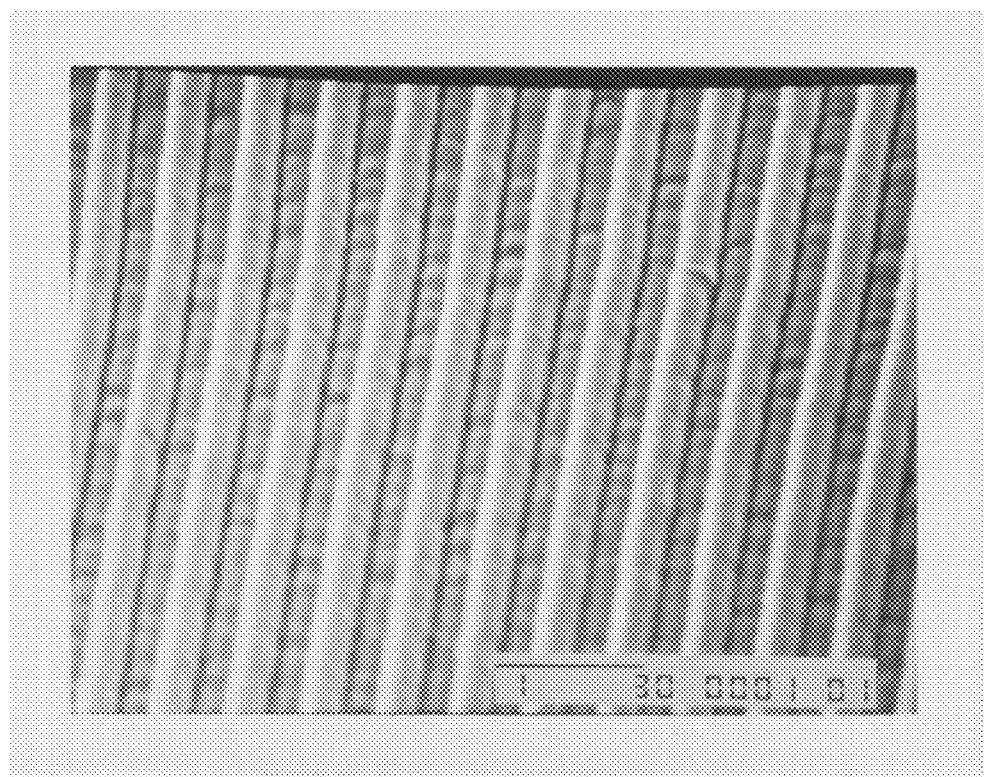

In addition to the methods described thus far, economic contact printing methods are attractive to imprint optical polymers with desired submicron grating patterns. A silicone grating stamp can be used to imprint the grating into a thin layer of UV curable optical adhesive (FIG. 11 (a)). A waveguide layer is then deposited on the top surface of the grating by sputtering with a thin layer of Si$_3$N$_4$ or other suitable media. Alternatively, the grating is coated with a high index spin-on TiO$_2$ polymer film to yield a high-quality resonant sensor element. An example of a contact printed grating is shown in FIG. 11 (b).

Dual-Mode TE/TM Polarized GMR Sensors

Figure 12:
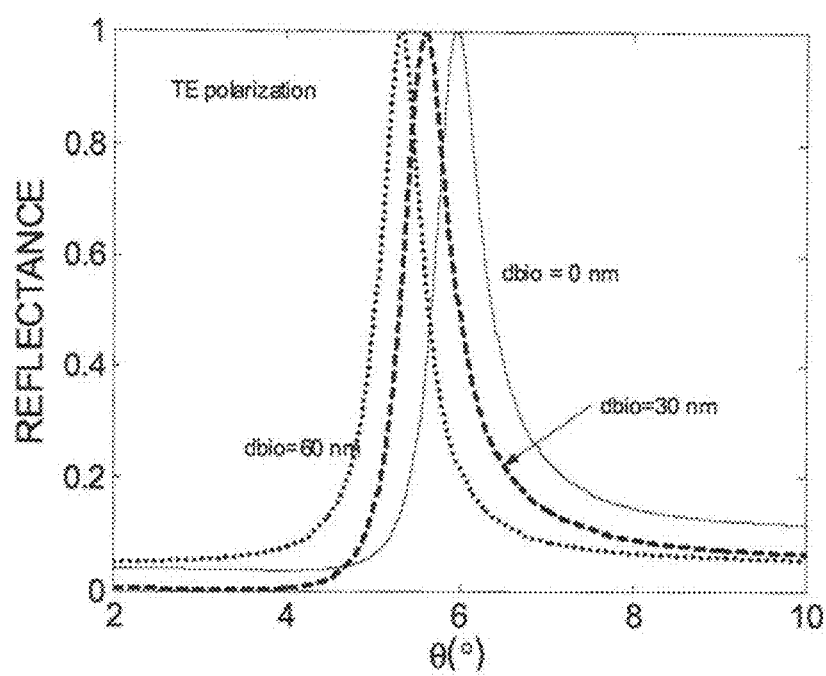
Figure 13:
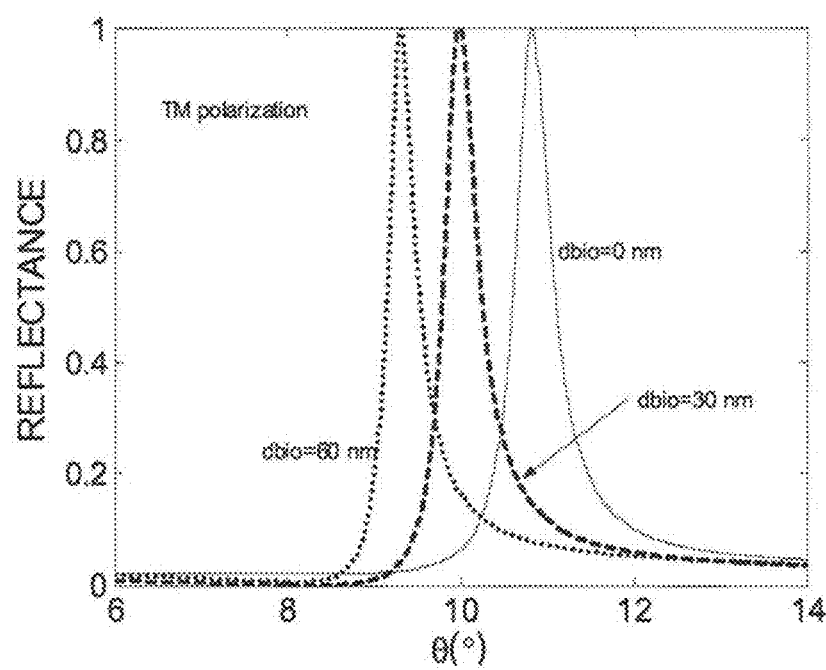
FIG. 13 shows the corresponding TM-polarization response.
Figure 14:
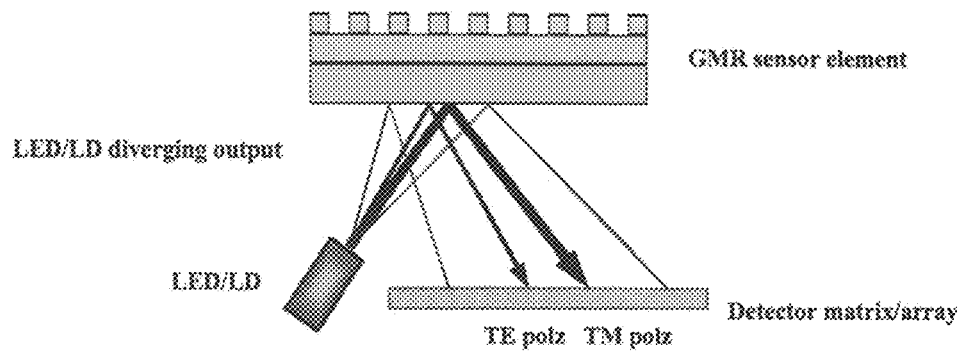
FIG. 14 is a schematic drawing of a proposed resonant sensor system with dual polarization detection. The diverging beam from a source such as an LED or LD or VCSEL is incident on the sensor at various angles simultaneously.

Simultaneous detection of the TE and TM resonance shift on biolayer attachment to the sensor can greatly improve the quality of the sensing operation. This permits accurate determination of the complete biolayer properties; that is refractive index and thickness. FIGS. 12 and 13 show computed results indicating the resonance shifts in angle for both polarizations. Indeed, the moderate angular TE/TM resonance separation, realizable with proper element design, enables simultaneous detection of the two signals on a linear detector array as indicated in FIG. 14 with a diverging illumination by a light emitting diode (LED, possibly filtered for spectral narrowing), or a vertical-cavity surface-emitting laser (VCSEL), or laser diode (LD) with $\lambda$=850 nm that automatically covers the angular range of interest. In this example, the interrogating light beam enters through a cover medium such as a fused silica or plastic sheet (refractive index $n_c$). The light distributions of interest appear as reflection peaks on the detector. This example illustrates use of a high-index polymer material serving as both the homogeneous layer and the periodic layer. This could be fabricated, for example, by using a silicone mold for grating formation in commercial TiO$_2$-rich, thermally, or UV, curable polymer medium that is spin coated on the support wafer. Alternatively, a high-index waveguide layer can be deposited on a support wafer and the periodic layer molded on top of it.

Figure 15:
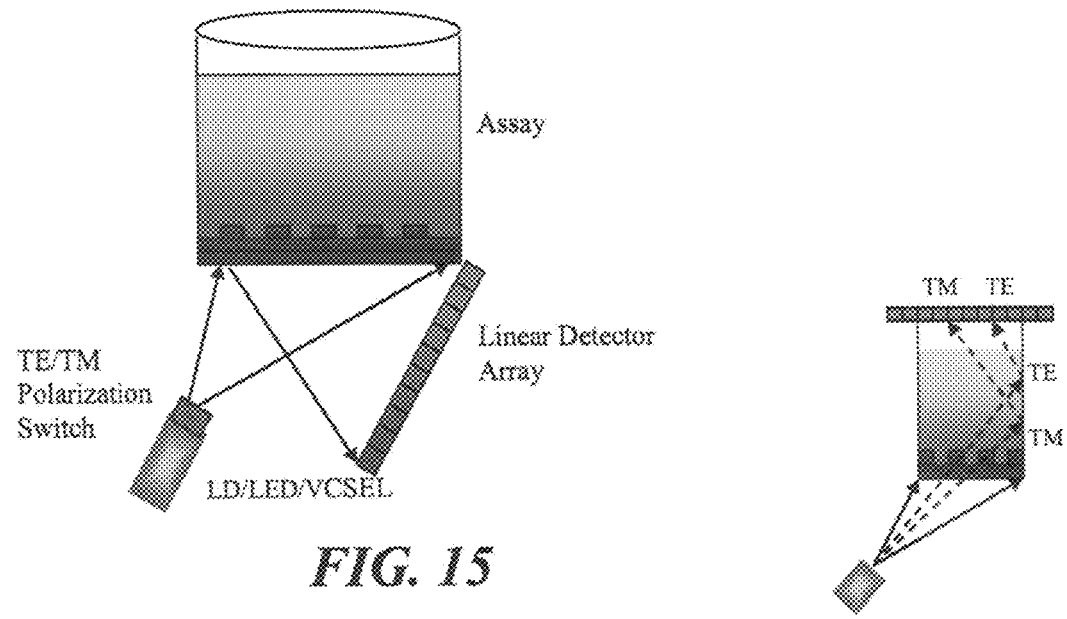
FIG. 15 gives an example GMR sensor embodiment with diverging input beam and associated detector employing polarization-diverse detection.
Figure 17:
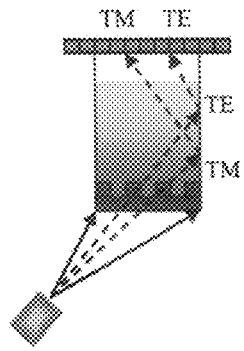
FIG. 17 explains polarized sensing in transmission mode where the TE peak (or minimum) and the TM peak (or minimum) are directed to the detector array aided by a reflection at a microwell wall.
Figure 16:
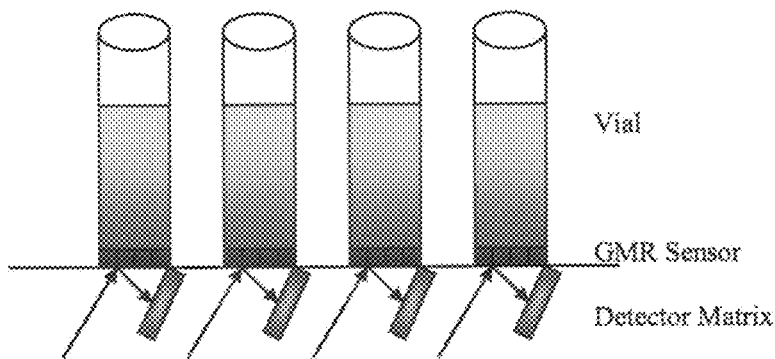
FIG. 16 is a schematic drawing of an arbitrarily-sized N×M array of microwells integrated with a GMR-sensor/detector unit as detailed in FIG. 15.

FIG. 15 illustrates an application of one embodiment of the present invention in a biomolecular sensing context. While unpolarized light will provide TE and TM resonance peaks on the detector array or matrix, the signal-to-noise (S/N) ratio can be improved by switching between the polarization states as indicated in FIG. 15 and scanning the detector for separate TE and TM signals temporally synchronized with the polarization switch. Moreover, to further enhance the S/N ratio, the light source can be equipped with a beam shaping element to sculpt the light distribution on the sensor in an optimal manner. In fact, in some applications, the use of a converging rather than diverging wavefront may be desired. Such beam shaping can, for example, be performed with appropriate holographic or diffractive optical elements. This allows wavefronts of arbitrary amplitude and phase distribution to be generated. FIG. 16 indicates use of the device in FIG. 15 in a multi-well system. In the pharmaceutical industry, microwell plates are used for effective drug compound screening in which this system application might find advantageous deployment. FIG. 17 illustrates an additional configuration where now the detector matrix is on top of the well and the transmitted nulls (or peaks) associated with TE and TM resonance are measured. As a biolayer adds to the sensor, the location of the nulls on the detector shifts to permit quantification of the binding event. In this example, the incident wave is at an angle and the signal recovery is aided by reflections off the microwell walls.

Figure 18:
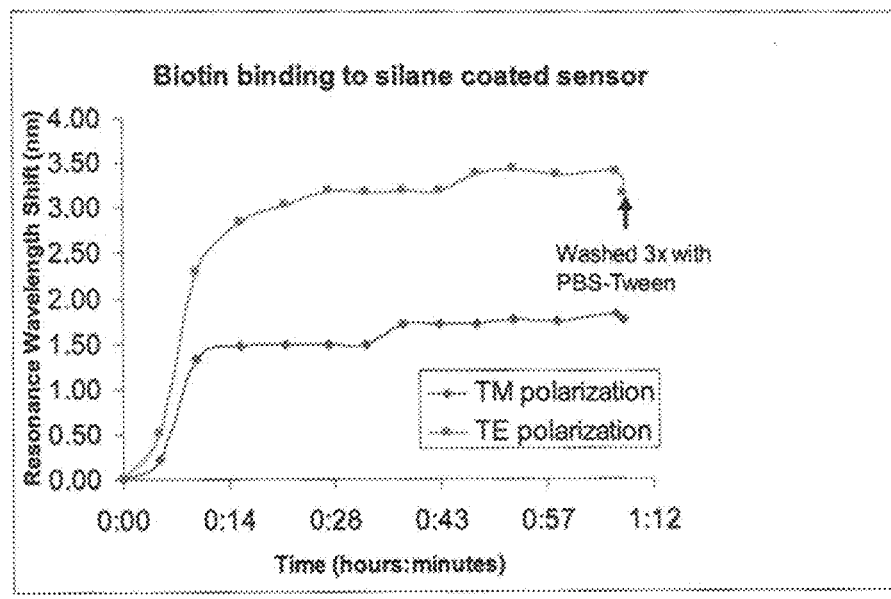
FIG. 18 is an illustration of the experimental use of GMR sensor polarization diversity to quantify biotin binding to a silane-coated sensor surface. The molecular attachment event is monitored as function of time. Results for both TE and TM polarizations are shown.

Preliminary experiments have demonstrated the polarization diversity feature of this technology, which supplies separate resonance peak shifts for each polarization (TE and TM), providing a means for high detection accuracy as discussed above. FIG. 18 shows an example result pertaining to a GMR biosensor application.

Bandpass GMR Sensors

Figure 19:
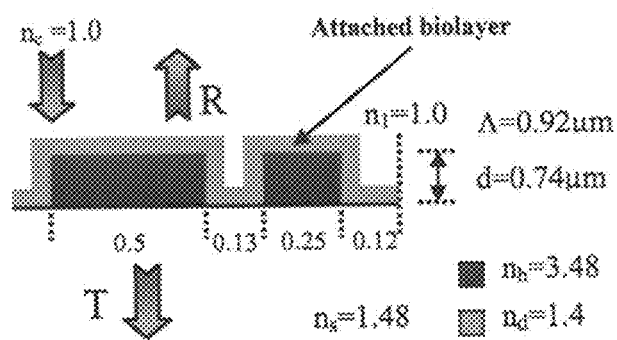
FIG. 19 shows an example element structure that achieves bandpass filter characteristics and thus realizes a GMR sensor operating in transmission. This element can be realized in the silicon-on-insulator (SOI) materials system.
Figure 20:
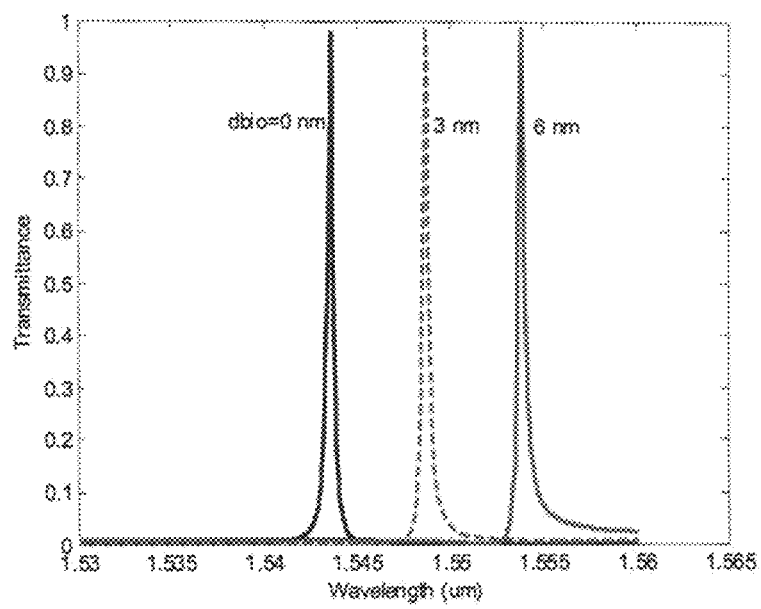
FIG. 20 provides computed transmission-type SOI resonant sensor spectra for different added biomaterial thicknesses. The sensor operates in air with the incident, reflected (R), and transmitted (T) waves as shown in FIG. 19. The incident wave is TM polarized in this example. The sensor design is shown in FIG. 19.

Transmission, or bandpass, resonance sensor elements can be fabricated in a variety of media including silicon-on-insulator (SOI), silicon-on-sapphire (SOS), and directly imprintable thermally-curable or UV-curable polymers. Formation of the periodic layer can be accomplished with traditional methods including e-beam writing and etching, holographic interferometry, and nanoimprint lithography with prefabricated masters. To clarify this embodiment, FIG. 19 shows a transmission sensor designed in an exemplary SOI structure. FIG. 20 illustrates the response of the sensor to addition of a biomolecular layer of thickness $d_{bio}$ to the sensor surface. The transmission peak alters its spectral location in a sensitive manner. This plot should be contrasted, for example, with the sensor in FIGS. 12-14 that operates in reflection. As the biomaterial attaches to the surface of the sensor, the resonance wavelength shifts substantially at a rate of ~1.6 nm spectral shift per nm added material. Note the particular profile design that achieves this performance in this case.

Planar Compact GMR Sensors and Arrayed Sensor Systems

For ease of fabrication and to reduce cost, we now disclose implementation of the embodiments of the present invention presented above in planar systems formats. The sensors will operate in transmission. Thus, the light enters the sensor that is in contact with a medium whose interaction with the sensor is of interest. The light travels across the medium to the detector on which a transmitted intensity minimum (bandstop filter) or intensity maximum (bandpass filter) is measured. Spatial shifts in the locations of these light distributions permit quantification of key features of the biomolecular binding reaction.

Figure 21:
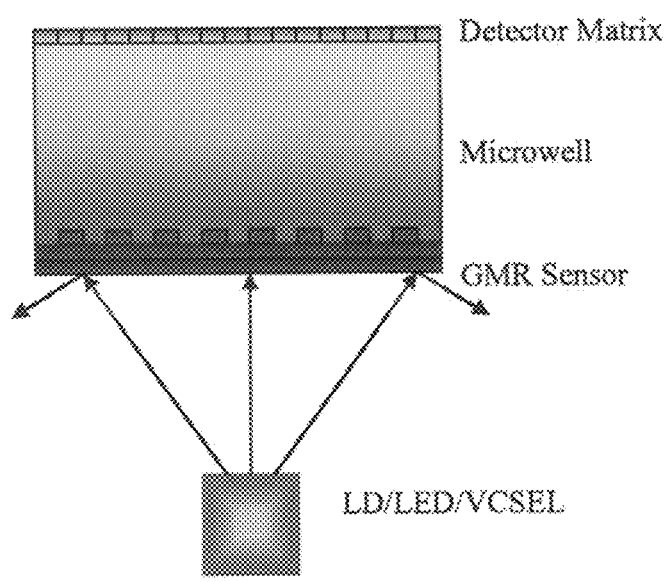
FIG. 21 depicts a sensor/detector configuration associated with sensing operation in direct transmission.
Figure 22:
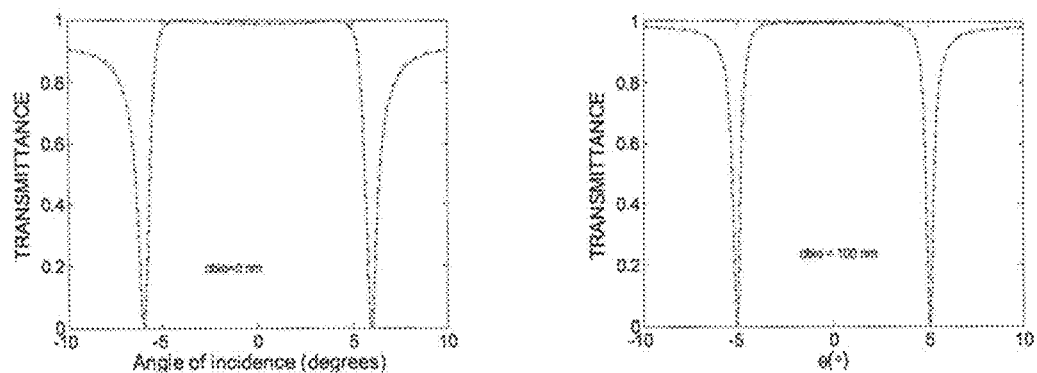
FIG. 22 gives calculated TE angular responses associated with a GMR sensor layout such as the one shown in FIG. 21 for different added thickness of biomaterials.
Figure 23:
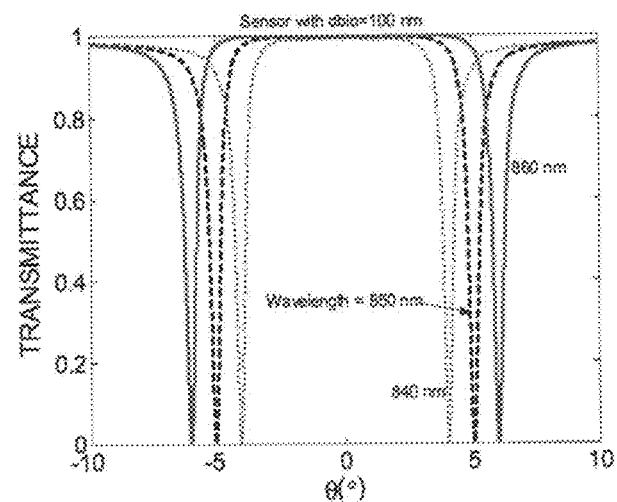
FIG. 23 shows calculated TE angular responses for the GMR sensor configuration in FIG. 21 for varying input wavelength to illustrate wavelength diversity. In this computation, $d_{bio}$=100 nm. The diverging input beam covers the angular range of interest automatically.

FIG. 21 illustrates this concept for a single sensor interrogated with a diverging beam from a laser diode (LD), a light-emitting diode (LED), or a vertical-cavity surface-emitting laser (VCSEL). A polarizing, beamshaping, or line-narrowing function can be integrated with the source as needed. The detector is placed on the opposite side of the sensing volume as shown. FIG. 22 shows the computed intensity distribution (signal) on the detector matrix for a GMR sensor operating in bandstop mode thus generating a peak in reflection and a concomitant minimum in transmission. The input wavelength is 850 nm in this example. Two minima appear at symmetric angular locations relative to the sensor normal, since the resonance wavelength at normal incidence differs from that for nonnormal incidence. The two simultaneous minima can be used to enhance the accuracy of the sensing operation as two angular shifts are acquired. In FIG. 22, for added biolayer thickness $d_{bio}$=0 the minima appear at θ~6° while for $d_{bio}$=100 nm the angular resonance is at θ~5° in this case. FIG. 23 illustrates wavelength diversity; that is, by tuning the input wavelength to a discrete set of wavelengths, additional data points can be gathered to improve accuracy in data analysis and fitting to numerical models. As the wavelength changes, so do the resonance angles and the light distributions on the sensors. Additionally, the wavelength controls the location of the minima on the detector furnishing flexibility in specifying the amount of detector area dedicated for each GMR sensor pixel in the sensor array.

Figure 24:
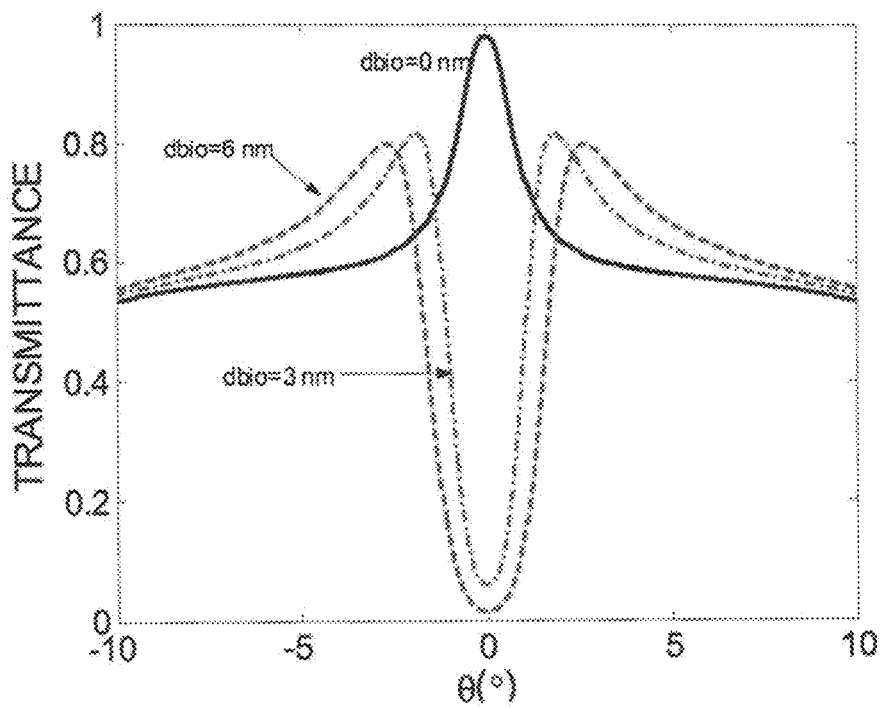
FIG. 24 gives calculated TM angular response of the GMR bandpass-type sensor shown schematically in FIG. 19 for differing biolayer thickness. The diverging input beam covers the angular range of interest automatically. Parameters are as in FIG. 19 and the input wavelength is set to λ=1.5436 μm in this example.

As explained in connection with FIG. 20, we have designed many resonant filters operating with transmitted peaks, that is as bandpass filters. In this case for a design such as that in FIG. 21, there would appear intensity maxima (rather than minima) on the detector array. Such transmission elements can be particularly effectively designed in high-refractive-index media such as silicon. FIG. 24 illustrates angularly diverse biosensing with a bandpass filter. By setting the wavelength such that the device sustains a transmission peak for the unperturbed surface, an ultra-high sensitivity arrangement is achieved. The most rapid change in the transmitted angular spectra occurs as the detuning by the biolayer buildup converts the sensor from a bandpass- to a bandstop state at normal incidence as shown in FIG. 24. Thus, sub-nanometer biofilm addition will be directly measurable by a simple intensity change on the detector on the output side. The shape of the forward transmitted light distribution received by the detector matrix is a sensitive function of the biolayer thickness as FIG. 24 clearly illustrates.

Figure 25:
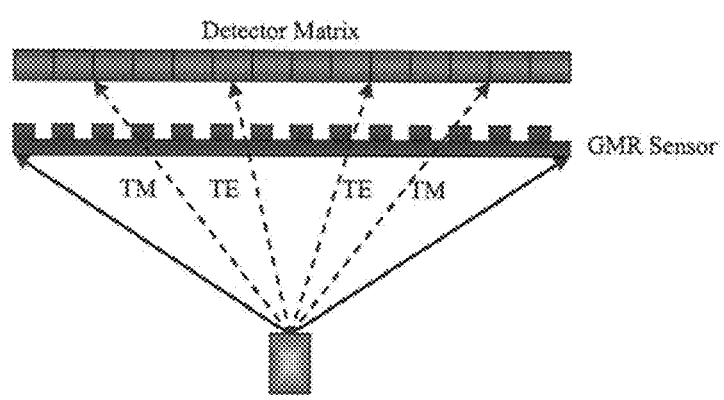
FIG. 25 shows a sensor/detector configuration associated with sensing operation in compact layout with direct, polarization-enhanced detection. The locations of TE and TM resonance nulls (or peaks) on the detector array are schematically indicated by the dashed arrows.
Figure 26:
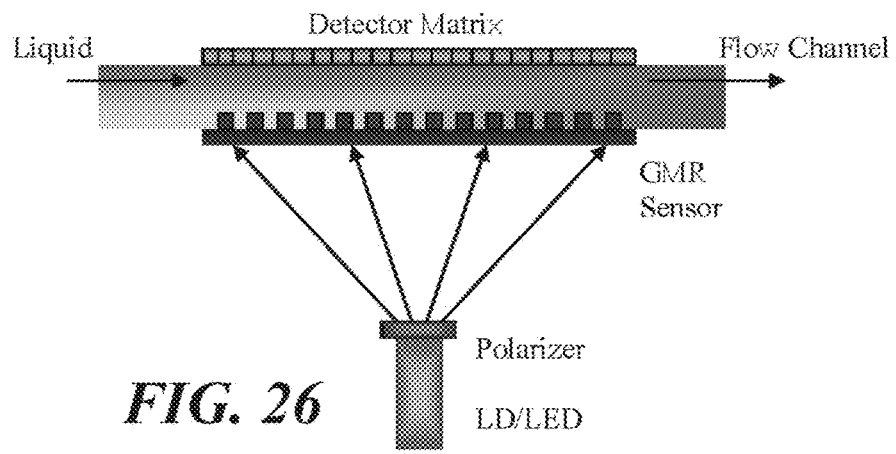
FIG. 26 illustrates a sensor/detector configuration associated with a sensing operation in direct transmission across a flow channel in a microfluidic bio- or chemical sensing system.

Yet another polarization diverse embodiment is shown schematically in FIG. 25 in which four simultaneous minima (or peaks) are monitored for high-precision biosensing. FIG. 26 provides an embodiment applicable to sensing in microfluidic systems.

In face of the growing number of biological and drug targets, there is an increasing need to invent new ways to profile chemical activity in massively parallel ways. Simultaneously, there is a need to reduce HTS expenses by dispensing minimal amounts of reagents for assays. Thus, there are developments in the industry towards nanoliter scale liquid dispensing. The GMR sensor technology disclosed herein is adaptable to meet these demands. The planar transmission formats indicated and explained above enable development of multichannel sensor systems. Existing and developing CCD and CMOS detector matrix technology with pixels down to 5-10 µm levels enables precision measurements of intensity distributions and their variations. Nanoimprint technology and precision thin-film methods enable fabrication of the requisite GMR sensor arrays. Molding methods are applicable for formatting and imposition of the larger features in these arrays.

Figure 27:
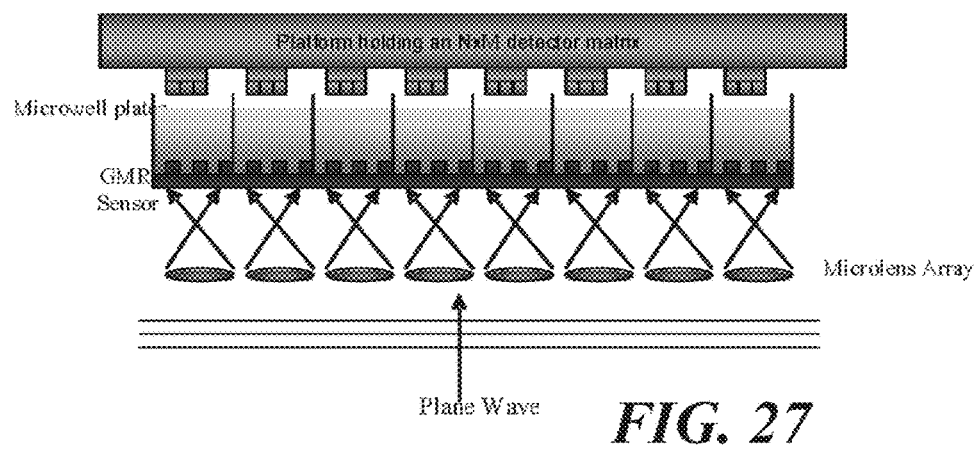
FIG. 27 shows an HTS platform with a single-source plane-wave input and wavefront shaping with a lens-array to implement angularly-addressable GMR sensor array without moving parts.
Figure 28:
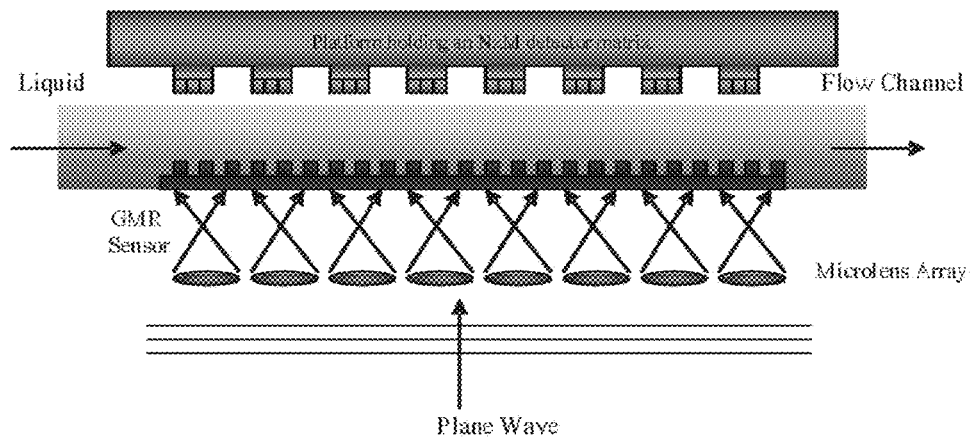
FIG. 28 is of an HTS platform with a single-source input and wavefront shaping with a lens-array to implement angularly addressable GMR sensor array in a microfluidic context.

FIG. 27 shows a system capable of parallel biosensing in accordance with the embodiments of the present invention set forth in the present disclosure. GMR sensors installed into microwell plates are addressed by angular spectra generated by conversion of an incident plane wave to spherical or cylindrical waves by appropriately-designed array of diffractive or refractive microlenses as shown in the figure. The detector array mounted above receives the signals to implement precision biosensing. FIG. 28 shows a similar operation where the sensors are stimulated by directed flow within flow channels in a microfluidic assembly; FIG. 28 omits the intricate channel construction and details associated with real microfluidic devices.

Figure 29:
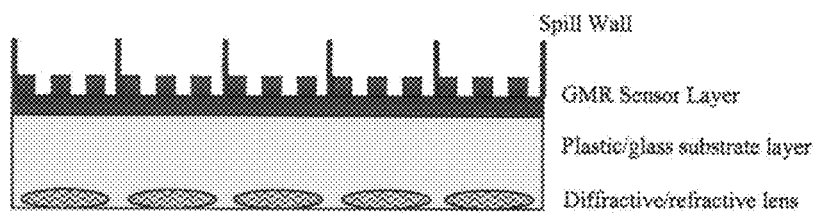
FIG. 29 indicates a GMR sensor array fabricated in plastic or glass media by imprinting and molding methods.
Figure 30:
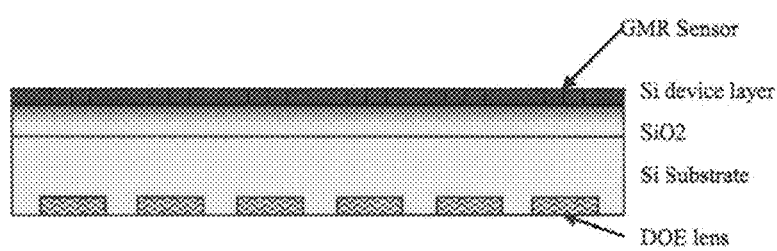
FIG. 30 is of a GMR sensor array fabricated in the silicon-on-insulator materials system.

Practical cost-effective GMR arrays can be fabricated in glass or plastic media. To give an example, diffractive or refractive lens arrays with given focal lengths and diameters on plastic substrates can be purchased economically from several vendors. On the blank side of the substrate, opposite the lens array, high-index spin-on $TiO_2$ polymer film is applied. The grating pattern is then imprinted with a specially designed silicone stamp with appropriate period as noted in FIG. 11, resulting in the GMR sensor. Spill walls to separate different solutions and to avoid cross-contamination can then be installed by molding methods. Alternatively, a high-index thin film is first deposited on the substrate with the grating pattern subsequently applied on top. The resulting GMR array is shown in FIG. 29. FIG. 30 shows a conceptual GMR array made in SOI to take advantage of existing silicon-based microfabrication methods.

Multimode GMR Sensors

Figure 31:
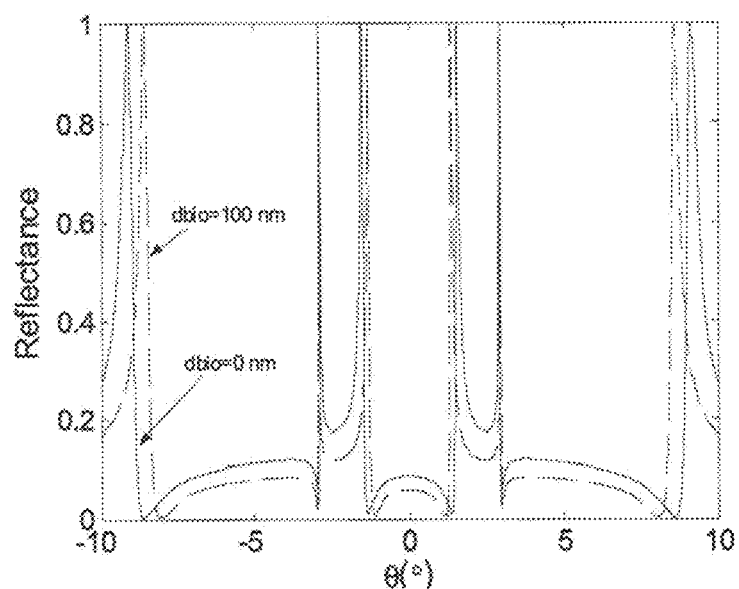
FIG. 31 provides calculated TE-reflectance angular response of a GMR multimode sensor for differing added thickness ($d_{bio}$) of biomaterials.
Figure 32:
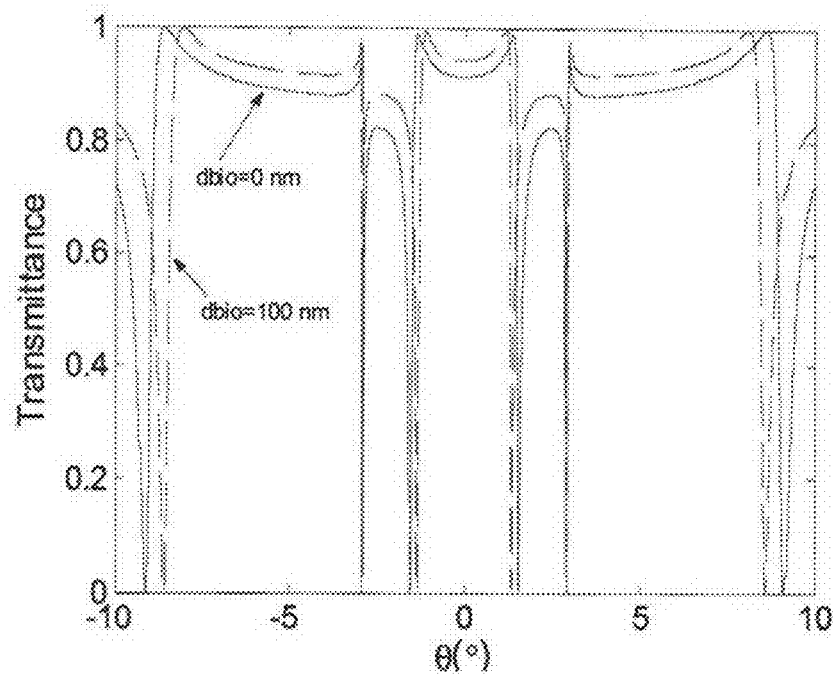
FIG. 32 provides calculated angular transmittance spectrum corresponding to the multimode sensor of FIG. 31.
Figure 33:
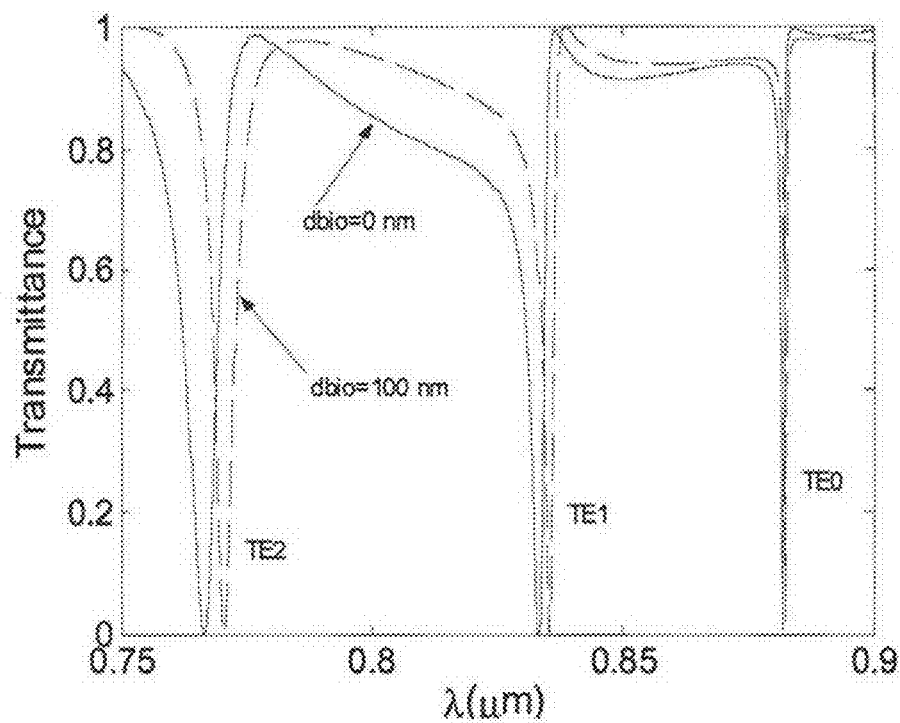
FIG. 33 shows a computed transmittance spectrum corresponding to the device parameters in FIG. 31 at normal incidence θ=0 exhibiting multimode resonance characteristics. This multimode biosensor operates with leaky modes $TE_0$, $TE_1$, and $TE_2$ in the wavelength range depicted. The highest sensitivity is provided by the $TE_2$ mode in this exemplary case.

Yet another approach to improve detection reliability is to increase the number of operational resonant leaky modes and thereby apply richer spectra for sensing and precision curve fitting. Thus, multiple resonance peaks due to presence of multiple waveguide modes can be generated and monitored. These multiple modes provide distinct spectral signatures that may be utilized in precision sensing. FIG. 31 shows the TE-polarization response of a double-layer GMR sensor with parameters as specified in the figure caption assuming no sidewall attachment. These parameters include the following: Calculated TE-reflectance angular response of a GMR multimode sensor for differing added thickness ($d_{bio}$) of biomaterials. Thicknesses $d_1=900$ nm (homogeneous layer), $d_2=270$ nm (grating layer); refractive indices $n_1=2.00$, $n_H=2.00$, $n_L=1.00$, $n_c=1.46$, $n_s=1.00$, $n_{bio}=1.40$; grating period $\Lambda=450$ nm; fill factor $f=0.5$, wavelength of incident light $\lambda=850$ nm. With fixed input wavelength, the reflectance spectrum exhibits several resonance peaks originating in different leaky modes. On addition of a biolayer, the spectrum responds with measurable change in the angular spectrum as shown in FIG. 31. This spectrum would be monitored in reflection, for example with the configuration in FIG. 16. FIG. 32 gives the corresponding transmission spectrum that would be monitored, for example, in the system of FIG. 27. FIG. 33 illustrates the wavelength spectrum for this sensor at normal incidence, indicating three leaky modes within the spectral band shown. On account of the particular distribution of the electromagnetic fields within this sensor, operation in the $TE_2$ mode gives highest sensitivity, that is, largest angular and spectral shifts per unit added thickness, as demonstrated in FIGS. 31-33.

Figure 34:
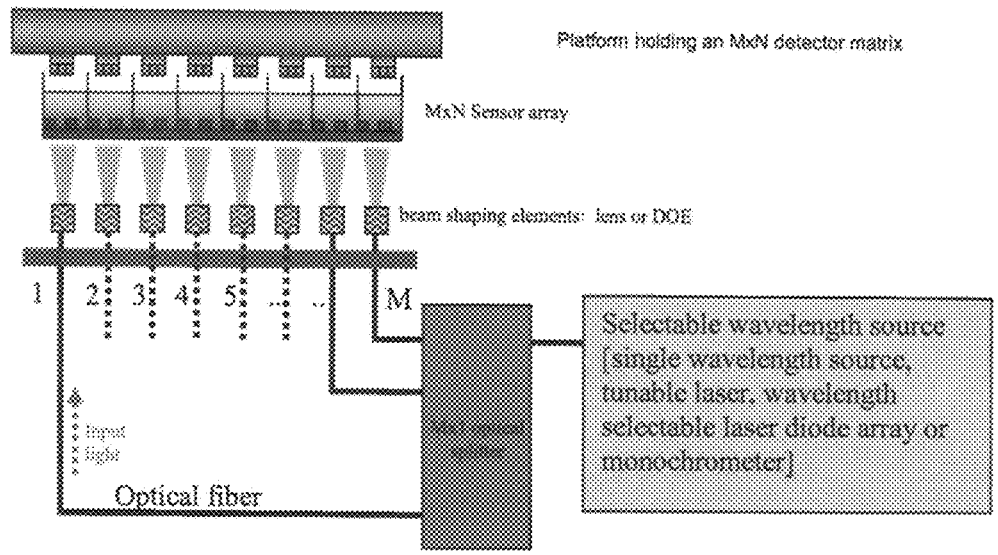
FIG. 34 depicts a single source system utilizing an optical splitter and optical fiber delivery.
Figure 35:
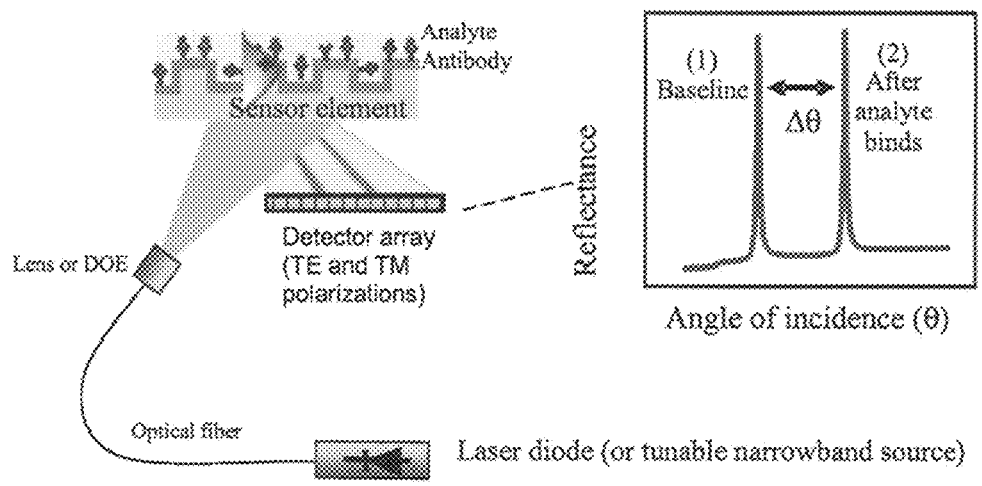
FIG. 35 depicts a single channel schematic illustration of a label-free guided-mode resonance sensor system for detecting chemical or biological analyte bonded to an antibody.
Figure 36:
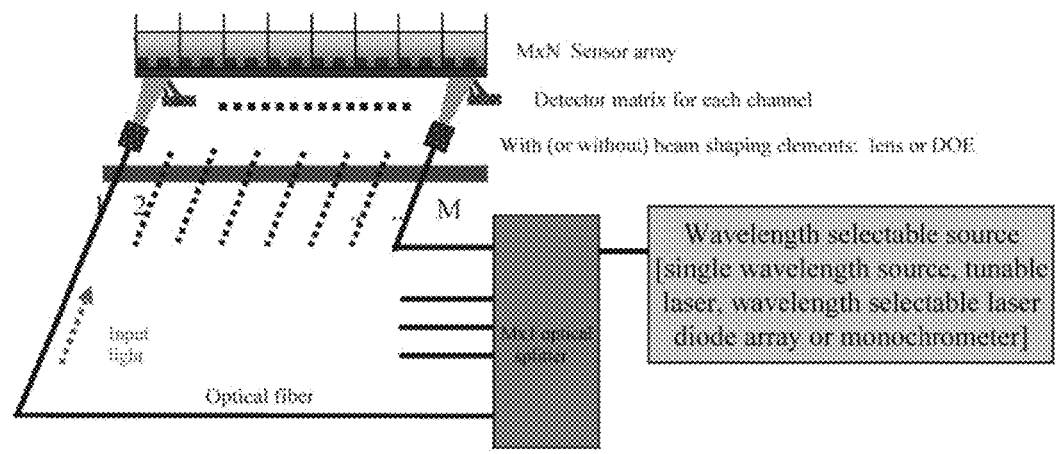
FIG. 36 depicts a reflection configuration utilizing an optical fiber array for light delivery.

Referring now to FIGS. 34, 35 and 36, and initially to FIG. 34 thereof, a sensor/detector configuration employing fiber coupled light delivery in a GMR sensor platform is depicted. FIG. 1 shows a single source system utilizing an optical splitter and optical fiber delivery. A single light source is split into "M" channels (with an optical splitter) and incident on the sensor array through optical fibers. The light exiting from each fiber is shaped by an integrated or external lens/DOE and is incident in free-space on the sensor element. Alternately, the diverging light exiting the optical fiber can be incident on the sensor element directly without the use of beam shaping elements. The optical fiber can be selected based on its numerical aperture or other properties as part of the system design. A polarizing element or polarization maintaining fiber can be used in the system to control the polarization state(s) incident on the sensor element. The incident wavelength can be tunable, thus allowing both angular and spectral tuning in a single system.

The system can be configured as a transmission system, where light transmitted through the sensor array is detected with a detector matrix on the opposite side of the array from the incident light, as depicted. The system can also be configured as a reflection system, where the light is incident on the array at an angle and the beam reflected from the array is measured with a detector matrix disposed on the same side of the array as the incident light.

FIG. 35 depicts a single channel schematic illustration of a label-free guided-mode resonance sensor system for detecting chemical or biological analyte bonded to an antibody. The antibody is depicted as a "Y" and the antibody is depicted as a ball in the cup of the "Y". The antibody should be selected based upon analyte or analytes to be detected. In some embodiments, bovine, llama or alpaca serum antibody and be used, although the invention is not limited to these antibodies.

In operation, the diverging beam from the fiber coupled laser diode is incident on the sensor with a continuous range of angles. As binding events occur at the sensor surface (by the analyte bonding with the antibody), resonance peak changes can be tracked as a function of incident angle. The resonance occurs at different angles for TE and TM polarization states of the input light, enabling high-accuracy, cross-referenced detection.

FIG. 36 shows s multiple channel array. It has a reflection configuration utilizing an optical fiber array for light delivery. The optical fiber array can also be scanned across a sensor array (for either reflection or transmission).

For example, to screen a M×N sensor array, an M-fiber array can be scanned across the bottom of N rows of sensor elements. The scanning can occur by (a) moving the fiber array+detector matrix across the sensor plate, or by (b) moving the sensor plate across the fiber array+detector matrix.

Figure 37:
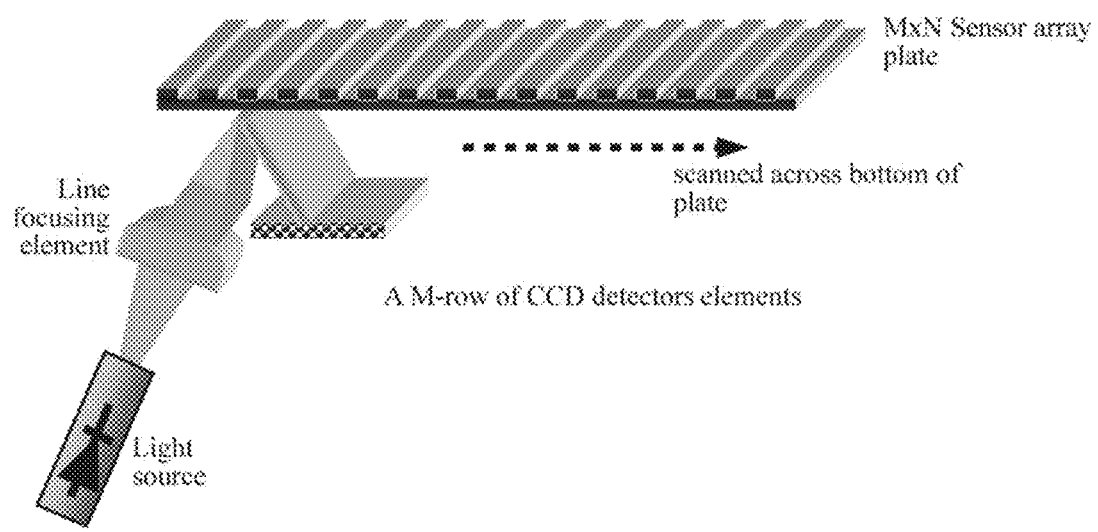
FIG. 37 depicts a reflection sensor system employing a scanning line source.

FIG. 37 depicts a sensor/detector configuration employing a scanning line source. Although FIG. 37 depicts a reflection sensor, however, it could also be configured as a transmission sensor by positioning the detector elements on the opposite side of the array plate as the incident light.

The optical source can be a single wavelength (or wavelength selectable) source that is shaped with a line focusing element (for example a cylindrical lens). The line focused light illuminates M-sensor elements simultaneously in the M×N sensor array. The reflected response is measured on a M-row of detector matrices (such as a row of CCD detector elements). The light line source and detector element assembly can be scanned across the bottom of a sensor plate to efficiently read a M×N sensor array. Note: The line focusing element also acts as the beam shaping element (i.e. can be diverging, converging or any designed wavefront).

The following additional embodiments are also contemplated:

A GMR sensor assembly comprising a waveguide structure configured for operation at or near one or more leaky modes of input light and a detector for TE and TM resonances having a sensor array with at least N×M sensor elements.

The GMR sensor assembly defined in paragraph 76 above, further comprising a refractive lens to shape the illuminating light.

The GMR sensor assembly defined in paragraph 76 above, further comprising an array of refractive lenses to shape the illuminating light.

The GMR sensor assembly defined in paragraph 76 above, further comprising a diffractive lens to shape the illuminating light.

The GMR sensor assembly defined in paragraph 76 above, further comprising means for determining the polarization state and waveshape characteristics of a wavefront of input light.

The GMR sensor assembly defined in paragraph 76 above, further comprising means for providing input light having at least two different wavelengths.

The GMR sensor assembly defined in paragraph 76 above, further comprising means for providing input light having at least first and second polarization characteristics.

The GMR sensor assembly defined in paragraph 76 above, further comprising means for detecting at least two resonant modes.

The GMR sensor assembly defined in paragraph 76 above, further comprising integrated microfluidic flow channels adjacent said waveguide structure.

The GMR sensor assembly defined in paragraph 76 above, further comprising a substrate, light conditioning elements, and microvials integrated into a transparent media.

The GMR sensor assembly defined in paragraph 76 above, wherein the array is disposed on an integrated media taken from the group of semiconductors, semiconductors/dielectric hybrids, semiconductor/dielectric/metal hybrids, and dielectrics.

The GMR sensor assembly defined in paragraph 76 above, wherein the arrayed sensor elements are physically separate from the illuminating source.

The GMR sensor assembly defined in paragraph 76 above, wherein and the arrayed sensor elements are integrated with the source of illuminating input light.

The GMR sensor assembly defined in paragraph 76 above, further comprising a readout detector in a compact biochip or microbench format.

A guided mode resonant sensor wherein the source of illumination is fiber or waveguide coupled.

A guided mode resonant sensor wherein the waveguide or optical fiber is selected by design to have a specific numerical aperture, polarization maintaining property or material specification.

A guided mode resonant sensor wherein the source of illumination is focused into a line using a line focusing element.

A guided mode resonant sensor wherein the source of illumination is focused into a line using a line focusing element comprising a cylindrical lens.

A guided mode resonant sensor wherein the source of illumination and detector elements are scanned across the sensor array.

A guided mode resonant sensor wherein a single light source is split into several channels using an optical splitter.

A guided mode resonant sensor having an array of optical fibers/waveguides are used to deliver light to an array of sensor elements.

It will further be understood from the foregoing description that various modifications and changes may be made in the preferred embodiment of the present invention without departing from its true spirit. This description is intended for purposes of illustration only and should not be construed in a limiting sense. The scope of this invention should be limited only by the language of the following claims.

What is claimed is:

1. A guided-mode resonance sensor assembly comprising:
a waveguide structure including a periodic structure, the waveguide structure being adapted to receive input light from a source of light onto the waveguide structure to cause two or more leaky TE resonant modes and/or two or more leaky TM resonant modes;
one or more photodetectors positioned to receive zero order diffracted light during non-control measurement of an analyte having disposed on said waveguide structure or in its immediate environment for detecting changes in one or more of the phase, waveshape and/or magnitude of resonances of at least two different TE guided modes and/or the resonances of at least two different TM guided modes to permit distinguishing between first and second physical states of said waveguide structure or in its immediate environment.

2. The guided-mode resonance sensor assembly defined in claim 1, wherein said guided-mode resonance sensor assembly is configured for operation where the input light includes diverging light.

3. The guided-mode resonance sensor assembly defined in claim 1, further comprising a beam-shaping element for forming an input wavefront of input light with known amplitude, and phase characteristics.

4. The guided-mode resonance sensor assembly defined in claim 1, wherein the source of illumination creating said input wavefront of input light is selected from the group of a light emitting diode, laser diode, vertical-cavity surface-emitting laser, and a filtered broadband source.

5. The guided-mode resonance sensor assembly defined in claim 1, further comprising means for applying a first known polarization state at a first known time and a second known polarization state at a second known time which can be the same as or different from said first known time,
and
means for analyzing TE and/or TM guided mode resonances respectively detected at said first and second known time to permit distinguishing between first and second physical states of said waveguide structure or its immediate environment.

6. The guided-mode resonance sensor assembly defined in claim 1, further comprising means for selectively inputting different wavelengths of input light into the waveguide structure.

7. The guided-mode resonance sensor assembly defined in claim 1, wherein the means for detecting is disposed such that the different TE and/or TM guided mode resonances to be detected are those reflected from the waveguide structure onto said means for detecting.

8. The guided-mode resonance sensor assembly defined in claim 1, wherein the means for detecting is disposed such that the different guided modes of TE and/or TM resonances to be detected are those transmitted through a plane through the waveguide structure and onto the means for detecting.

9. The guided-mode resonance sensor assembly defined in claim 1, wherein the means for detecting is a matrix of photodetector elements.

10. The guided-mode resonance sensor assembly defined in claim 1, wherein the sensor is configured to operate with more than one resonant leaky modes.

11. The guided-mode resonance sensor assembly defined in claim 1, further comprising a holographic diffraction element for diffracting the input light.

12. The guided-mode resonance sensor assembly defined in claim 1, wherein the detection means receives the different guided modes of TE and/or TM resonances at an arbitrary angle.

13. The guided-mode resonance sensor assembly defined in claim 1 wherein the means for detecting changes in one or more of the phase, waveshape and/or magnitude of said different TE and/or TM guided mode resonances comprises sensor array with at least N×M sensor elements.

14. The guided-mode resonance sensor assembly defined in claim 13, wherein the input light has known magnitude and phase characteristics.

15. The guided-mode resonance sensor assembly defined in claim 13, wherein the N×M sensor elements configured for illumination by a single light source input through a light shaping port.

16. A GMR sensor assembly comprising:
a waveguide structure configured for operation at or near one or more leaky modes of input light, said waveguide structure or its immediate environment having physical properties subject to change over time,
a polarization switch in the path of the input light permitting alternate measurements of the spatial positions of TM and TE resonances at different times
a detector for TE and TM resonance positioned to receive zero order diffracted light during non-control measurement of an analyte disposed on said waveguide structure or in its immediate environment and having a sensor array with at least N×M sensor elements, where N is at least 1 and M is at least 2 and
an analyzer for determining the physical state of said analyte based upon the spatial position of said TE and TM resonances considered together.

17. The GMR sensor assembly defined in claim 16, wherein the input light has known magnitude and phase characteristics.

18. The GMR sensor assembly defined in claim 16, wherein the N×M sensor elements configured for illumination by a single light source input through a light shaping port.

* * * * *